US00PP33206P2

(12) United States Plant Patent
Mathey

(10) Patent No.: US PP33,206 P2
(45) Date of Patent: Jun. 29, 2021

(54) ***HYDRANGEA* 'SMNHSC'**

(50) Latin Name: ***Hydrangea serrata* x *macrophylla***
Varietal Denomination: SMNHSC

(71) Applicant: Spring Meadow Nursery Inc., Grand Haven, MI (US)

(72) Inventor: Megan Mathey, Holland, MI (US)

(73) Assignee: Spring Meadow Nursery, Grand Haven, MI (US)

( * ) Notice: Subject to any disclaimer, the term of this patent is extended or adjusted under 35 U.S.C. 154(b) by 0 days.

(21) Appl. No.: 17/039,261

(22) Filed: Sep. 30, 2020

(51) Int. Cl.
*A01H 6/48* (2018.01)
*A01H 5/02* (2018.01)

(52) U.S. Cl.
USPC ..... Plt./250

(58) Field of Classification Search
USPC ..... Plt./250
See application file for complete search history.

*Primary Examiner* — Annette H Para
(74) *Attorney, Agent, or Firm* — Cassandra Bright

(57) ABSTRACT

A new and distinct cultivar of *Hydrangea* plant named 'SMNHSC' is disclosed, characterized by floriferous, mounding plants producing abundant mophead inflorescences. Plants produce strong lavender colored colors when treated with aluminum sulfate, strong pink colored flowers when untreated. Reblooming occurs rapidly. The new variety is a *Hydrangea*, normally produced as an ornamental plant.

4 Drawing Sheets

Latin name of the genus and species: *Hydrangea serrata* x *macrophylla*.

Variety denomination: 'SMNHSC'.

BACKGROUND OF THE INVENTION

The new *Hydrangea* cultivar is a product of a planned breeding program conducted by the inventor, at a commercial nursery in Grand Haven, Mich. The objective of the breeding program was to produce new *Hydrangea* varieties with new colors, and strong stems. The cross resulting in this new variety was made during July of 2014.

The seed parent is the variety *Hydrangea serrata* 'MAK20', U.S. Plant Pat. No. 24,820. The pollen parent is *Hydrangea macrophylla* 'SMNHMSIGMA' U.S. Plant Pat. No. 26,929. The new variety was identified as a potentially interesting selection in the Summer of 2016 at a commercial greenhouse in Grand Haven, Mich. Date of first public offer was Jun. 23, 2020, occurring in the United States. This offer was made directly by the inventor or one who obtained the claimed invention directly or indirectly from the inventor. This sale and all public disclosures made between Jun. 23, 2020 and the filing of this application fall within the exception allowed under 102(b)(1).

Asexual reproduction of the new cultivar 'SMNHSC' by vegetative softwood cuttings was first performed during the Summer of 2016, at a commercial greenhouse in Grand Haven, Mich. Subsequent asexual propagation has shown that the unique features of this cultivar are stable and reproduced true to type in four successive generations.

SUMMARY OF THE INVENTION

The cultivar 'SMNHSC' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNHSC' These characteristics in combination distinguish 'SMNHSC' as a new and distinct *Hydrangea* cultivar:

1. Fast reblooming.
2. Mophead inflorescence.
3. Strong lavender flower color when treated with aluminum sulfate, strong pink flower color untreated.
4. Attractive mounding plant habit.

PARENT COMPARISON

Plants of the new cultivar 'SMNHSC' are similar to plants of the seed parent in most horticultural characteristics, however, plants of the new cultivar 'SMNHSC' differ in the following;

1. The new variety has a mophead inflorescence, while the seed parent has a lacecap inflorescence.
2. The new variety produces single sterile sepals while the seed parent produces double sterile sepals.
3. The new variety has lighter green foliage than the seed parent.

Plants of the new cultivar 'SMNHSC' are similar to plants of the pollen parent in most horticultural characteristics, however, plants of the new cultivar 'SMNHSC' differ in the following;

1. The new variety has a lighter pink flower than the darker pink-red of the pollen parent.
2. With aluminum treatment the new variety has a lighter purple flower than the darker blue-purple flower of the pollen parent.

COMMERCIAL COMPARISON

Plants of the new cultivar 'SMNHSC' can be compared to the variety *Hydrangea macrophylla* 'Bailmer', U.S. Plant Pat. No. 15,298. These varieties are similar in most horticultural characteristics; however 'SMNHSC' differs in the following:

1. The new variety has more intense flower color than this comparator.
2. The new variety has stronger stems than this comparator.
3. The new variety has larger leaves than this comparator.

Plants of the new cultivar 'SMNHSC' can be compared to the variety *Hydrangea serrata* 'SMNHSDD', U.S. Plant Pat. No. 29,832. These varieties are similar in most horticultural characteristics; however 'SMNHSC' differs in the following:

1. The new variety has mophead inflorescences, while this comparator is lacecap.
2. The new variety is more floriferous than this comparator.
3. The new variety has narrower leaves than this comparator.
4. Flowers of the new variety are pink or lavender, depending up treatment with aluminum sulfate; flowers of this comparator are blue.

BRIEF DESCRIPTION OF THE PHOTOGRAPHS

'SMNHSC' is illustrated by the accompanying photographs which show the plant's form, foliage, and inflorescences. The colors shown are as true as can be reasonably obtained by conventional photographic procedures. Colors in the photographs may differ slightly from the color values cited in the detailed botanical description, which accurately describe the colors of the new hybrid *Hydrangea*. Age of the plants photographed is between 2 to 3 years.

FIG. 1 shows container grown plants of 'SMNHSC' grown in a greenhouse in Grand Haven, Mich. in 2019 at about 2 years. Plants on the right of the photo have lavender inflorescences and have been treated with a typical acidic "bluing"(aluminum sulfate) treatment. Pink flowering plants on the left have not been give the "bluing" treatment.

DETAILED BOTANICAL DESCRIPTION

Figure 1:
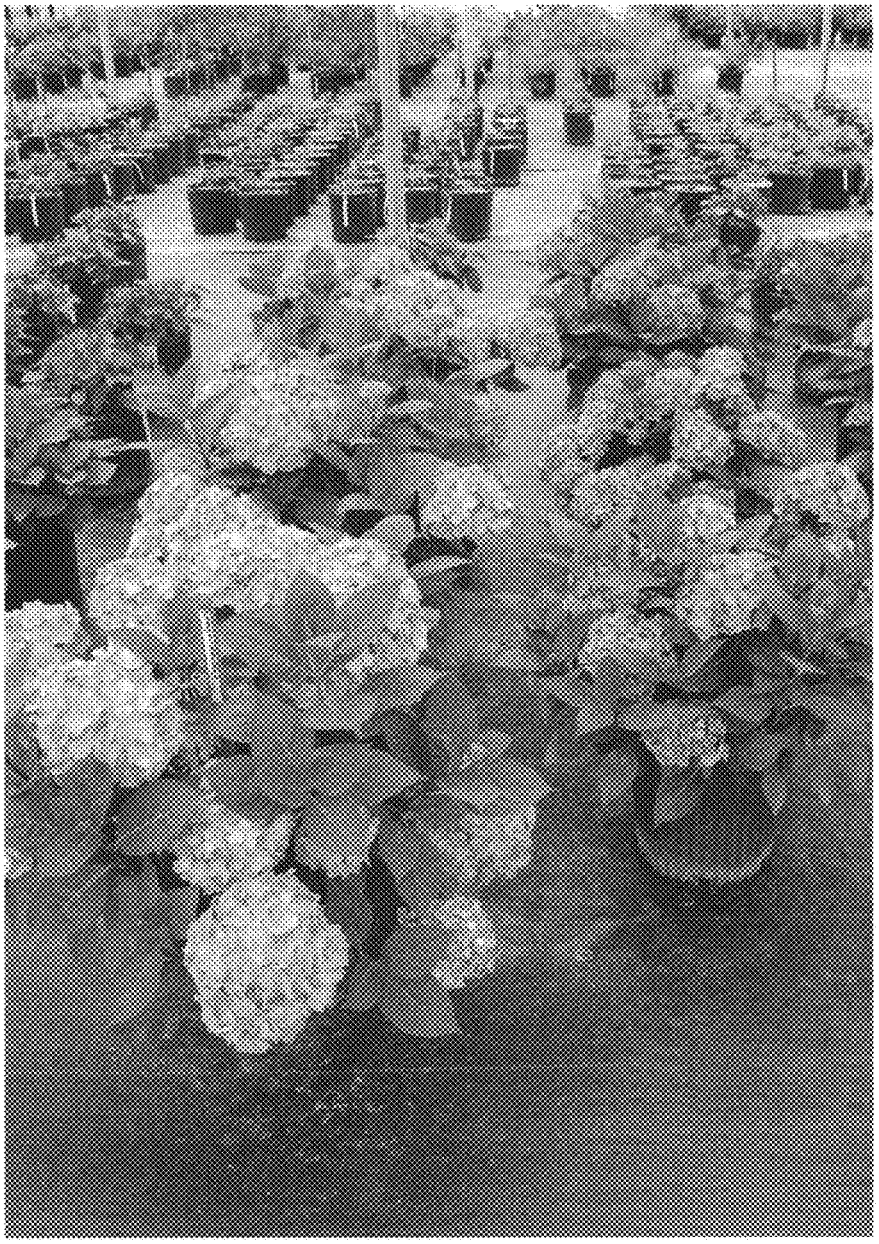
Figure 2:
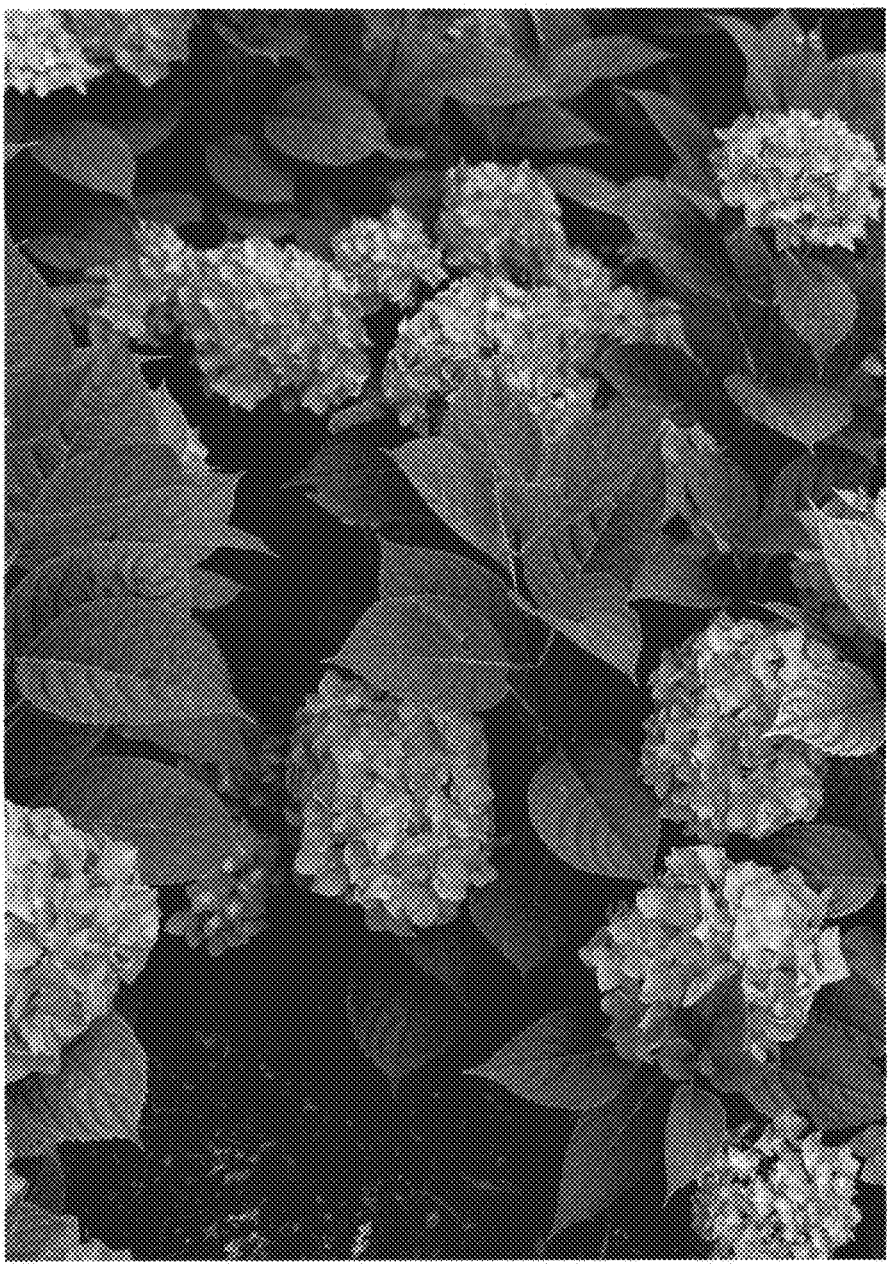
FIG. 2 shows a field grown plant of 'SMNHSC' with inflorescences in various stages. No "bluing" treatment was given.
Figure 3:
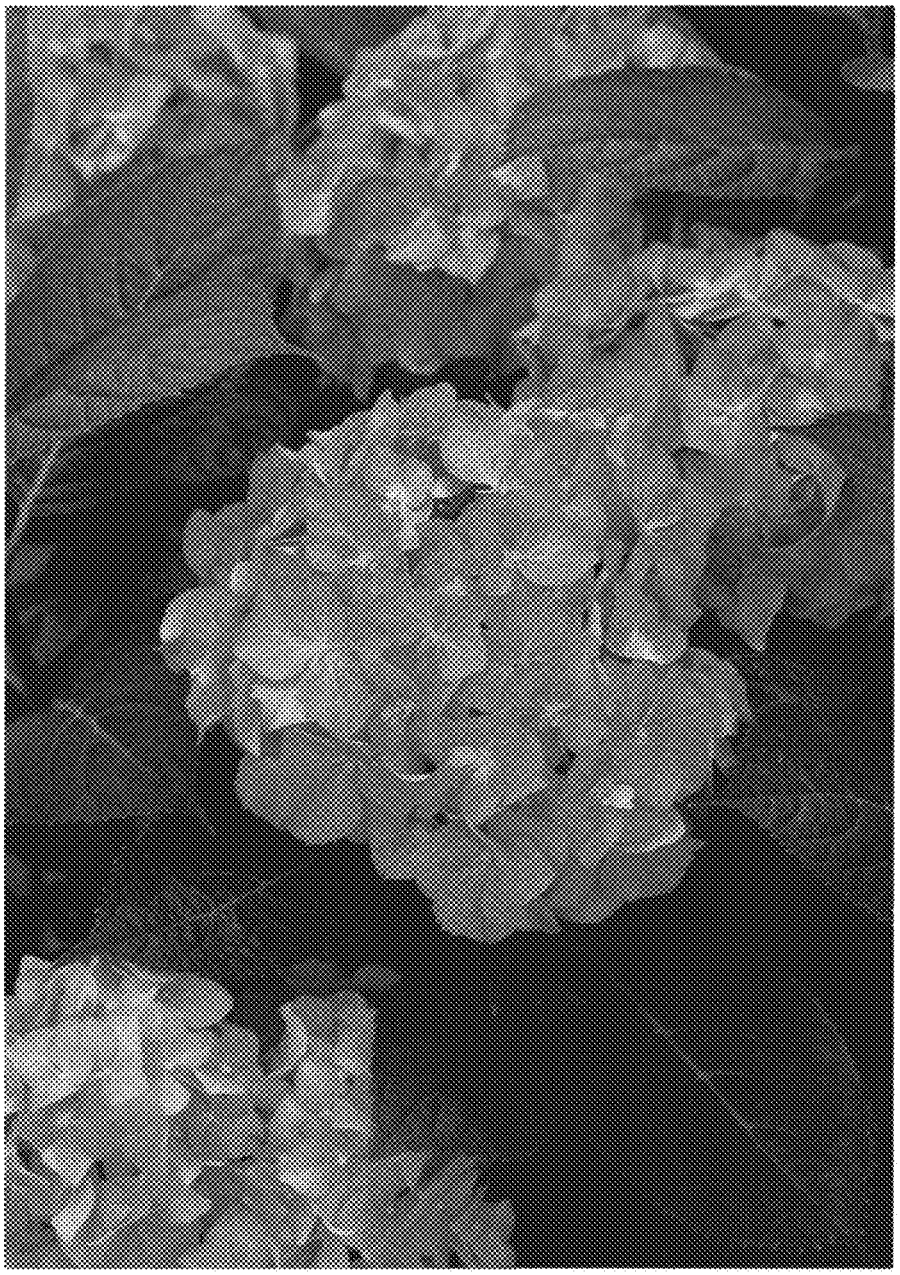
FIG. 3 shows the mature inflorescence of a container-grown plant, treated without "bluing" treatment, grown in a greenhouse in Grand Haven, Mich. in 2019.
Figure 4:
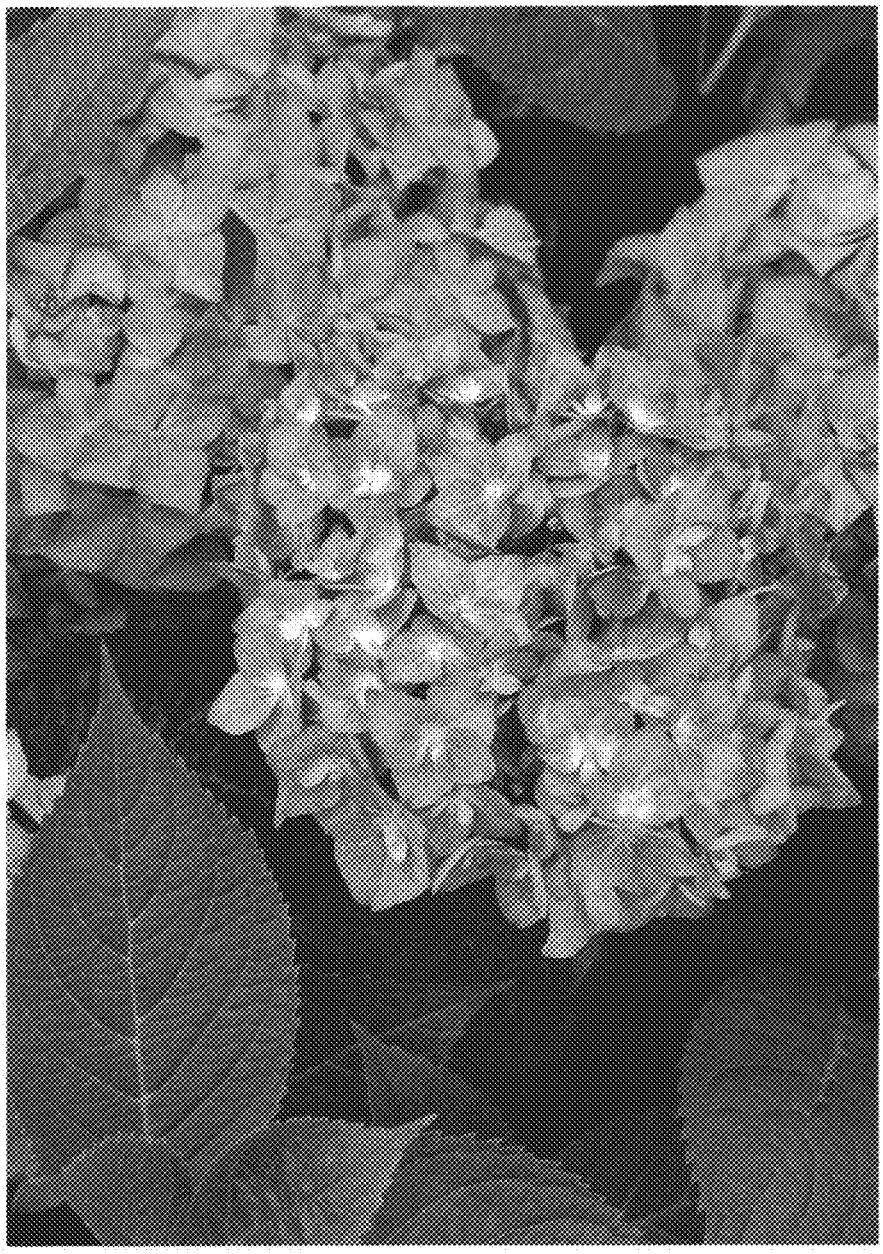
FIG. 4 shows the mature inflorescence of a container-grown plant, treated with a typical acidic "bluing"(aluminum sulfate) treatment, grown in a greenhouse in Grand Haven, Mich. in 2019.

In the following description, color references are made to The Royal Horticultural Society Color Chart 2015 except where general terms of ordinary dictionary significance are used. The following observations and measurements describe 'SMNHSC' plants grown in a commercial poly greenhouse in Grand Haven, Mich. under natural lighting. Measurements were taken during Summer of 2020. The plants were about 2.5 years old, growing in 3-gallon containers. The growing temperature ranged from 18° C. to 27° C. during the day and from 5° C. to 10° C. during the night. Measurements and numerical values represent averages of typical plant types.

Botanical classification: *Hydrangea serrata* x *macrophylla* 'SMNHSC'.

PROPAGATION

Time to initiate roots: Approximately 10 days at about 20° C.

Time to produce a rooted young plant: Approximately 30 days at about 20° C.

Propagation method: Softwood cuttings.

PLANT

Plant type: Flowering deciduous perennial shrub.

Age of plant described: Approximately 2 to 3 years old.

Growth habit: Upright and outward.

Overall plant shape: Mounding.

Height: 45 cm.

Plant spread: 80 cm.

Growth rate: Moderate.

Plant vigor: Vigorous.

Branching habit: Basal, lateral branching increases with pinching. Branches upward and outward.

Length of primary lateral branches: 43 cm.

Diameter of lateral branches: 5 mm.

Quantity of lateral branches: About 50.

Stem:

*Stem shape.*—Round.

*Stem strength.*—Strong.

*Color.*—Immature: RHS Yellow-Green 144B. Mature: RHS Greyed-Brown 199B.

*Pubescence.*—None.

*Aspect.*—Straight, at angles of 15° to 35° from center.

*Lenticels.*—Not observed.

Internode length: Average 3 cm.

Root description: Fleshy and fibrous roots present. Moderately dense, free branching, medium to thick main roots with fine, fibrous secondary roots. Main roots colored near Brown 200D, secondary roots near Yellow-White 158D.

FOLIAGE

Leaf:

*Arrangement.*—Opposite.

*Leaf shape.*—Elliptic.

*Average length.*—16.5 cm.

*Average width.*—6.5 cm.

*Apex.*—Acuminate.

*Base.*—Obtuse.

*Margin.*—Serrate.

*Texture of top surface.*—Glabrous.

*Texture of bottom surface.*—Rough with distinct veins.

*Leaf pubescence.*—None.

*Color.*—Young foliage upper side: RHS Green 139A. Young foliage under side: RHS Greyed-Green N189A. Mature foliage upper side: RHS Grey Green N189A. Mature foliage under side: RHS Green NN137C.

*Venation.*—Pattern: Pinnate. Color upper side: RHS Yellow-Green N144D. Color under side: RHS Yellow-Green 145A.

*Petiole.*—Average Length: 2 cm. Diameter: 3 mm. Petiole color upper side: RHS Yellow Green N144D.

Petiole color lower side: RHS Yellow Green 145A. Petiole Texture upper side: Glabrous. Petiole Texture lower side: Glabrous.

FLOWER

Natural flowering season: Summer.
Inflorescence:
*Type*.—Mophead.
*Quantity of flowers per inflorescence*.—Fertile flowers: 10-20. Sterile flowers: 50.
*Persistent or self-cleaning*.—Persistent, self-cleaning after several weeks.
*Longevity*.—Individual flowers stay fresh on the plant for about 2 weeks. Inflorescences are ornamental for several weeks.
*Fragrance*.—None detected.
Panicle:
*Shape*.—Broad orbicular.
*Height*.—8.5 cm.
*Diameter*.—13 cm.
Sterile flower:
*Bud shape*.—Spherical.
*Bud length*.—2 mm.
*Bud diameter*.—2 mm.
*Bud color*.—Acidic: RHS Violet-Blue 91B. Basic: RHS Red-Purple 70D.
*Flower aspect*.—Upright and outwards.
*Flower arrangement*.—Rotate.
*Flower length*.—8 mm.
*Flower diameter*.—8 mm.
*Persistence*.—Persistent.
Sterile flower petals:
*Petal arrangement*.—Whorl, overlapping.
*Quantity*.—5.
*Length of petal*.—3 mm.
*Width of petal*.—1.5 mm.
*Apex*.—Acute.
*Shape of petal*.—Ovate.
*Petal margin*.—Entire.
*Petal base*.—Cuneate.
*Petal texture*.—Smooth, upper and under side.
*Color*.—Upper surface at first opening: Acid: RHS Violet-Blue 97A. Basic: RHS Red-Purple 70D. Under surface at first opening: Acid: RHS Violet-Blue 97A. Basic: RHS Red-Purple 70D. Upper surface at maturity: Acid: RHS Violet-Blue 97A. Basic: RHS Red-Purple 70D. Under surface at maturity: Acid: RHS Violet-Blue 97A. Basic: RHS Red-Purple 70D.
Sterile flower sepal:
*Arrangement*.—Single overlapping whorl.
*Number*.—5.
*Shape*.—Obovate.
*Tip*.—Acute.
*Base*.—Oblique.
*Margin*.—Entire with some serrations near the apex.
*Length*.—Average 17 mm.
*Width*.—Average 21 mm.
*Texture, upper*.—Smooth.
*Texture, lower*.—Smooth.
*Color*.—Upper surface at first opening: Acidic: Mix of Red-Purple 70C and Purple Violet N82C. Flushed Violet-Blue 98B near margins. Basic: RHS Red-Purple 67C with White NN155A in the center. Under surface at first opening: Acidic: Mix of Red-Purple 70C and Purple Violet N82C. Flushed Violet-Blue 98C near margins. Basic: RHS Red-Purple 67C with White NN155A in the center. Upper surface at maturity: Acidic: Mix of Red-Purple 70C and Purple Violet N82C. Flushed Violet-Blue 98B near margins. Basic: RHS Red-Purple 67C with White NN155A in the center. Under surface at maturity: Acidic: Mix of Red-Purple 70C and Purple Violet N82C. Flushed Violet-Blue 98B near margins. Basic: RHS Red-Purple 67C with White NN155A in the center.
Sterile flower pedicel:
*Length*.—2.0 cm.
*Diameter*.—1 mm.
*Angle*.—About 45° from vertical.
*Strength*.—Flexible.
*Texture*.—Slightly pubescent.
*Color*.—Acidic: RHS Violet-blue 91B to Red-Purple 73B. Basic: RHS Red-Purple 73B.
Fertile flower:
*Bud shape*.—Orbicular.
*Bud length*.—4 mm.
*Bud diameter*.—4 mm.
*Bud color*.—Acidic: RHS Blue 108B. Basic: RHS Red-Purple 73B.
*Flower aspect*.—Upright and outward.
*Flower shape*.—Single whorl.
*Flower diameter*.—10 mm.
*Flower length*.—10 mm.
*Flower depth*.—6 mm.
*Longevity*.—1 to 2 weeks.
*Persistence*.—Self-cleaning.
Fertile flower petals:
*Arrangement*.—Whorl.
*Quantity*.—5 to 8.
*Length of petal*.—4 mm.
*Width of petal*.—2 mm.
*Apex*.—Acute.
*Base*.—Cuneate.
*Shape of petal*.—Ovate.
*Petal margin*.—Entire.
*Petal texture*.—Smooth, upper and under side.
*Color*.—Upper surface at first opening: Acidic: RHS Blue 100C. Basic: RHS Red-Purple 65B. Under surface at first opening: Acidic: RHS Blue 100C. Basic: RHS Red-Purple 65B. Upper surface at maturity: Acidic: RHS Blue 100C. Basic: RHS Red-Purple 65B. Under surface at maturity: Acidic: RHS Blue 100C. Basic: RHS Red-Purple 65B.
Fertile flower sepal:
*Arrangement*.—Whorled.
*Number*.—5 to 6.
*Shape*.—Deltate.
*Tip*.—Acute.
*Base*.—Truncate.
*Margin*.—Entire.
*Length*.—1 mm.
*Width*.—1 mm.
*Texture, upper*.—Smooth.
*Texture, lower*.—Smooth.
*Color*.—Upper surface at first opening: RHS Yellow-White 158D. Under surface at first opening: RHS Yellow-White 158D. Upper surface at maturity: RHS Yellow-White 158D. Under surface at maturity: RHS Yellow-White 158D.

Fertile flower pedicel:

*Angle.*—45°.

*Strength.*—Strong.

*Length.*—5 mm.

*Width.*—1 mm.

*Texture.*—Pubescent.

*Color.*—Acidic: RHS Violet-Blue 96A. Basic: RHS Red-Purple 63B.

REPRODUCTIVE ORGANS

Sterile flowers:

Androecium:

*Stamens.*—Number: 8. Filament length: 4 mm. Filament color: Acid: RHS Purple-Violet 91A. Basic: RHS Red-Purple 73C.

*Anthers.*—Shape: Round. Length: 1 mm. Color: Acid: RHS Violet-Blue 95C. Basic: RHS Green-White 157D. Pollen color: Green-White 157D. Pollen amount: Scant to moderate.

Gynoecium:

*Pistil.*—Number: 1. Length: 2 mm. Stigma: Shape: Globose. Color: Acid: RHS Purple 77C. Basic: RHS Red-Purple 69C.

Fertile flowers:

Androecium:

*Stamens.*—Number: Average 12. Filament length: 6 mm. Filament color: Acid: RHS violet-Blue 96C. Basic: RHS Red-Purple 68B Anthers: Shape: Globular. Length: 1 mm. Color: RHS Violet-Blue 94D. Pollen color: RHS Yellow-White 158C. Pollen amount: Moderate.

Gyonoecium:

*Pistil.*—Number: 1. Length: 2 mm. Style: Length: 1 mm. Color: RHS Yellow-White 158C. Stigma: Shape: Globose. Color: RHS Yellow-White 158C.

OTHER CHARACTERISTICS

Seeds and fruits: None observed.

Disease/pest resistance: Neither resistance nor susceptibility to normal diseases and pests of *Hydrangea* have been observed.

Temperature tolerance: Low temperature to −32° C. High temperature to 36° C.

What is claimed is:

1. A new and distinct cultivar of *Hydrangea* plant named 'SMNHSC' as herein illustrated and described.

* * * * *